Figure 1:
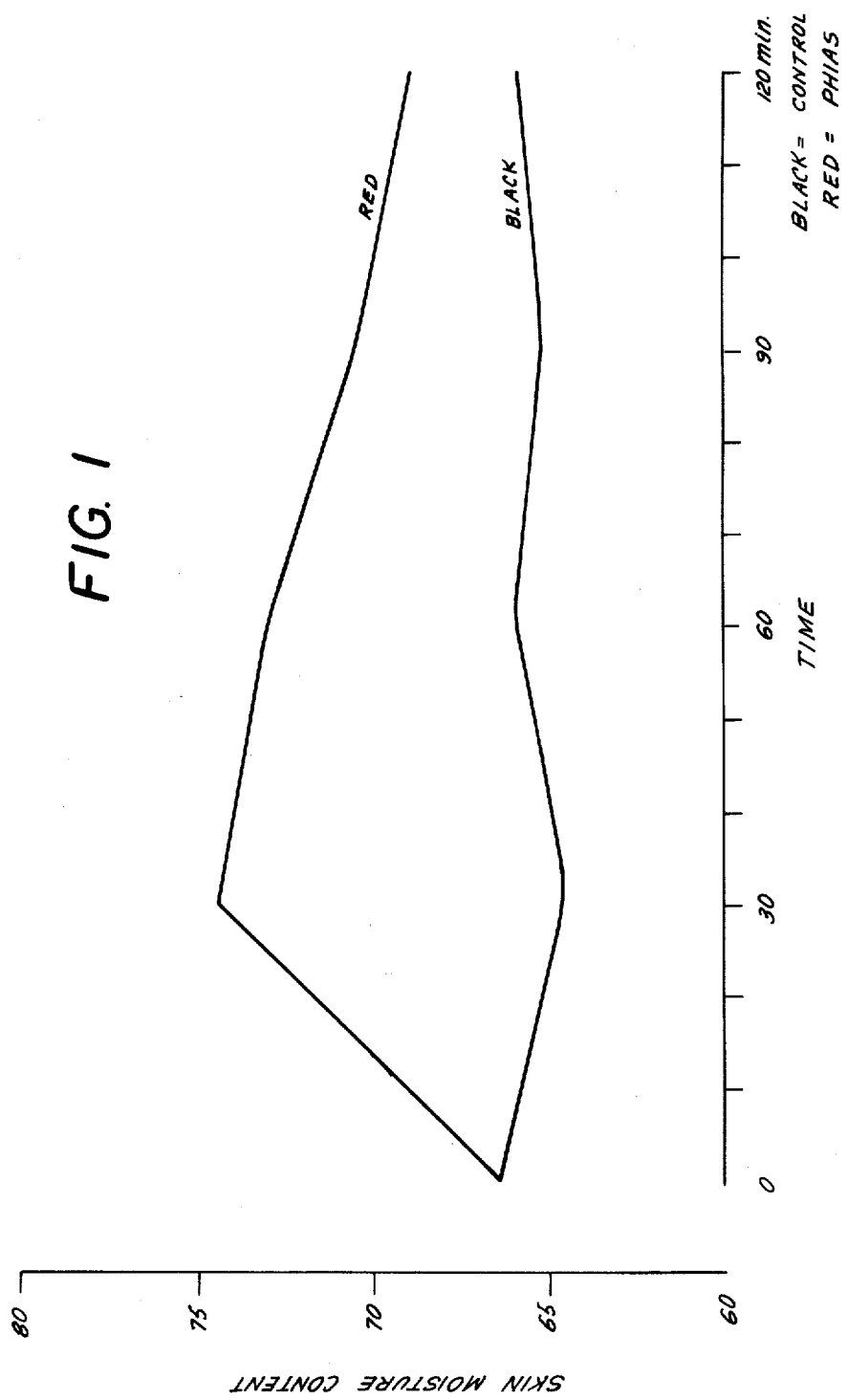

United States Patent [19]

Guillon

[11] 4,386,067
[45] May 31, 1983

[54] COSMETIC COMPOSITIONS

[75] Inventor: Claude Guillon, Neuilly sur Seine, France

[73] Assignee: Expanscience, Courbevoie, France

[21] Appl. No.: 172,118

[22] Filed: Jul. 25, 1980

Related U.S. Application Data

[63] Continuation-in-part of Ser. No. 71,600, Aug. 31, 1979, abandoned, which is a continuation of Ser. No. 869,078, Jan. 13, 1978, abandoned, which is a continuation of Ser. No. 783,129, Mar. 31, 1977, abandoned, which is a continuation of Ser. No. 646,092, Jan. 2, 1976, abandoned, which is a continuation of Ser. No. 472,574, May 23, 1974, abandoned, which is a continuation of Ser. No. 13,790, Feb. 24, 1970, abandoned.

[30] Foreign Application Priority Data

Apr. 30, 1969 [FR] France ............................. 69 13859

[51] Int. Cl.$^3$ .................. A61K 35/12; A61K 35/407; A61K 47/00; A61K 7/48
[52] U.S. Cl. ..................................... 424/95; 424/107; 424/364; 424/59; 424/64
[58] Field of Search .................... 424/364, 59, 64, 95, 424/107, 237

[56] References Cited

U.S. PATENT DOCUMENTS

| | | | |
|---|---|---|---|
| 2,205,925 | 6/1940 | Hickman | 424/237 |
| 2,221,690 | 11/1940 | Hickman | 424/237 |
| 2,276,531 | 3/1942 | Wechsler | 424/237 |
| 2,380,414 | 7/1945 | Buxton | 424/237 |
| 2,516,112 | 7/1950 | Freiman | 424/237 |

FOREIGN PATENT DOCUMENTS

| | | | |
|---|---|---|---|
| 4174M | of 1965 | France | 424/195 |
| 4194M | of 1965 | France | 424/195 |
| 4195M | of 1966 | France | 424/195 |

OTHER PUBLICATIONS

Chem. Abs. (I), vol. 32, item 3908$^9$, 1938.
Chem. Abs. (II), vol. 46, item 6414$^b$, 1952.
Chem. Abs. (III), vol. 46, item 8291, 1952.
Hilfer, Drug & Cosmetic Industry, vol. 76, pp. 627, 717-718 (1955).
Capella et al., J. Amer. Oil Chemists Soc. vol. 37, pp. 564-567, 1960.
Hoffmann et al., J. Amer. Oil Chemists Soc. vol. 39, pp. 323-327 (1962).
Harry, "Cosmetic Materials", vol. 2, pp. 20-21, 52-53, 57-58, 117-118, 155-158, 163-164, 305-306, 315-316, 405-406, Chem. Pub. Co. N.Y. 1963.
Wells et al., "Cosmetics and the Skin", p. 605, Reinhold Pub. Co. N.Y., 1964.
Chemical Abstracts, vol. 64, item 16155$^h$, 1966.

*Primary Examiner*—Donald B. Moyer
*Attorney, Agent, or Firm*—Alan H. Levine

[57] ABSTRACT

This invention relates to improved cosmetic compositions. It has been found that cosmetic compositions can be improved by adding to the formula a non-saponifiable fraction of an animal or vegetable oil. An animal or vegetable oil may also be present in the cosmetic composition, in which case it is preferably present in an amount below the conventional quantity and the non-saponifiable fraction is present in an amount at least equal to the amount of non-saponifiable material which would be extracted from the omitted portion of the animal or vegetable oil.

7 Claims, 2 Drawing Figures

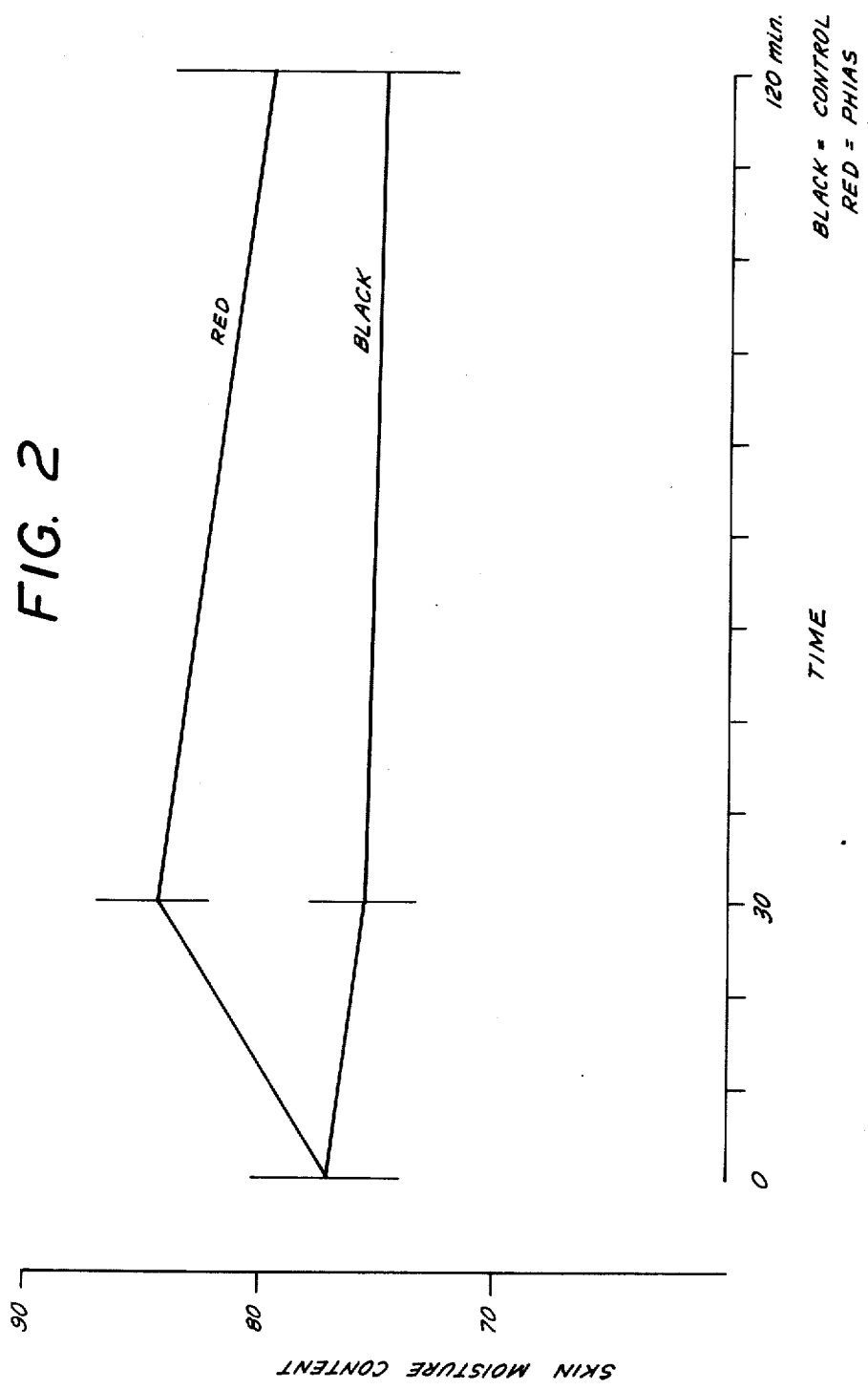

ing application Ser. No. 71,600, filed Aug. 31, 1979,
COSMETIC COMPOSITIONS

This application is a continuation-in-part of copending application Ser. No. 71,600, filed Aug. 31, 1979, now abandoned, which was a continuation of application Ser. No. 869,078, filed Jan. 13, 1978 now abandoned, which was a continuation of Ser. No. 783,129, filed Mar. 31, 1977 now abandoned, which was a continuation of application Ser. No. 646,092, filed Jan. 2, 1976 now abandoned, which was a continuation of application Ser. No. 472,574, filed May 23, 1974 now abandoned, which was a continuation of application Ser. No. 13,790, filed Feb. 24, 1970 also now abandoned.

This invention relates to cosmetic compositions.

It has long been known that vegetable and animal oils can be used for beauty-care purposes, and modern formulations for cosmetic products traditionally include oils of this kind.

However, I have determined that considerably more advantageous cosmetic compositions can be obtained by incorporating in the compositions of this kind non-saponifiable fractions of vegetable or animal oils either instead of or along with the oils themselves.

It is known that a vegetable or animal oil contains predominating quantities of fatty acid glycerides and non-glyceride substances and, in particular, a non-saponifiable fraction.

It has been shown that the nature of the fatty acids is substantially the same in all the oils, the proportions of these acids being variable, while the non-saponifiable fraction is characterized by the type of oil from which it is extracted. Accordingly, it is generally believed that the differences in dermatological properties which exist between the various oils is not solely attributable to the difference in the proportions of fatty acids but are primarily due to the differences in the nature of the non-saponifiable fractions.

It should be noted that it is not possible precisely to specifically identify an oil by its non-saponifiable fraction rather than by its fatty acid content, since the composition of the non-saponifiable fractions are most complex and are not entirely known. In many instances the non-saponifiables contain at least thirty different components some of which have a chemical composition that heretofore have remained undetermined.

It has been possible to characterize squalene, $\beta$-carotene and carotenoids, aromatic compounds, $C_{16}$ to $C_{32}$ hydrocarbons for the majority of unsaturated compounds, vegetable sterols ($\beta$-sitosterol, stigmasterol, campesterol, brassicasterol and other unknown sterols) or animal sterols, terpenes and free terpene alcohols ($\beta$-amyrine, butyrospermol, cyclo-artenol), $C_{12}$ to $C_{20}$ aliphatic alcohols and tocopherols.

Non-glyceride substances of vegetable oils have also been found to contain phospholipides and fatty acid esters of phytosterols and terpene alcohols and aliphatic alcohols. It is pointed out, however, that the esterifying fatty acids are different from those of the glycerides.

Whereas the non-glyceride substances of an oil can make up as much as 10% of the composition, the non-saponifiable substances constitute a minor proportion of from 0.1% to about 5% in the case of vegetable oils, and from 0.1% to about 50% in the case of animal oils.

The incorporation of non-saponifiable fractions of vegetable or animal oils instead of the oils themselves in cosmetic preparations in accordance with the invention has several advantages.

Thus, many of the constituents, such as the sterols and the aliphatic and terpene alcohols, which are present in the oil in their natural state in the combined form are restored to their free form by extraction of the non-saponifiable fraction and hence are more active or are provided with a different activity.

On the other hand, the active product concentration (non-saponifiable fraction) is measurably increased in relation to that which is possible with conventional preparations in which the active principle is in the form of the corresponding oil. This is because the conventional cosmetic formulation only provides for a small quantity of the active product to be incorporated; the other constituents being waxes, fatty alcohols, mineral oils, emulsifiers, preservatives, water, etc. The proportion of the active product, i.e., the non-saponifiable fraction, in contact with the skin during each application is thus very low. The incorporation of 1 gram of a non-saponifiable fraction of certain oils in 100 grams of a cosmetic formulation corresponds to the quantity of non-saponifiable fraction present in 300 grams of the corresponding oils. Thus, under the same conditions, the application of a composition according to the invention deposits on the skin a quantity of the active non-saponifiable fraction several hundred times greater than that deposited by application of a conventional composition containing only the corresponding oil.

In addition, in view of the low percentages of non-saponifiable fractions present in conventional cosmetic formulations, it is possible to include several non-saponifiable fractions of different oils in different proportions so as to benefit from the particular properties of each. By contrast, in conventional preparations, the inclusion of several different oils resulted in no real practical significance because the proportion of each oil was too low to have any beneficial effect.

Among the oils commonly used in cosmetic preparations, there may be mentioned the following oils whose non-saponifiable fractions are of particular interest. This list while extensive is not limited to be all inclusive; carob bean oil, palm oil, cabbage palm oil, coconut oil, sunflower seed oil, grapeseed oil, black mustard oil, ocilet oil, shea butter, and sweet almond oil, soya-bean oil, avocado oil, peanut oil, cottonseed oil, sesame oil, olive oil, maize oil, coconut butter, castor oil, Ben oil, linseed oil, colza oil, annato oil, cornseed oil, safflower oil, walnut oil, hazelnut oil and rapeseed oil; and among the animal oils: horsehair oil, mink oil, turtle oil, whale oil, fish oil, fish-liver oil, soft-roe oil, neat's-foot oil, tallows (bovine, equine, procine, ovine) and egg oil.

Tests on human beings have confirmed the effect of these non-saponifiable fractions in cosmetic preparations intended to restore the physiological equilibrium of the skin.

One very significant example is provided by formulations containing the non-saponifiable fraction of avocado oil associated with the non-saponifiable fraction of soya-bean oil which enhances the activity of the avocado oil non-saponifiable fraction.

Studies were conducted at the Heidberg General Hospital in Hamburg-Langenhorn, Germany, by A. Winkler to determine with the aid of the dermatometer the moisture content in the upper layer of human skin before and after treatment with a formulation made in accordance with the invention. The formulation selected referred to as PHIAS, was of the following:

Avocado Oil non-saponifiable fraction: 0.67 g
Soy bean Oil non-saponifiable: 1.33 g
Hexyl laurate: 48.60 g
Avocado Oil: ad 100.00 g As no water was present in the formulation, any increased moisture measured on the skin after application of the formulation was attributed to the ability of the formulation to draw moisture from the deeper cell layers. The test was conducted and the results obtained as follows:

Procedure

The tests were carried out according to the procedure described by BINGMER, WINKLER and WAGENER. The PHIAS preparation was tested in the original form as delivered by the manufacturer without any modification or dilution. A pre-test was first carried out to obtain fundamental indications about possible lines of action. To this effect, 4 volunteers were gathered, to whom the preparation was applied once, and after 30, 60, 90 and 120 minutes the effect was compared using a dermatometer with a control area.

The main test was then carried out on a group of 7 persons to whom PHIAS was applied once daily during 1 week on the inside of the lower third of the left or right forearm on an area of approximately 8×8 cm. The quantity used was about 0.2 ml each time, rubbed on the skin during one minute. Distilled water was rubbed on the control area of the other forearm.

Immediately before each rubbing, the existing moisture content was measured with the dermatometer, and noted on the graduations of the BINGMER apparatus. Measurements were made again 30 and 120 minutes after rubbing. The measuring head was carefully cleaned with dry cotton-wool.

When the tests were ended, the values obtained on the different days were divided into pre-values, 30-minute-values and 120-minute values, the mean and standard deviation were calculated and the difference for the 30- and 120-minute values vis-a-vis the control values was evaluated (red curve=PHIAS; black curve=control).

Results

Pre-Test

The result is given in FIG. 1 and Table 1. Given the small number of cases, the dispersion is not shown in the figure. However, it can be seen clearly that even in the small group, while the control areas remain at a constant value for a long time, a distinct increase in the existing water content of the skin appears with PHIAS, with a maximum at 30 minutes. The decrease until 120 minutes appears almost linear; it seemed therefore enough to use the values corresponding to 30 and 120 minutes after application.

The results obtained after the main test are given in Table 2 and FIG. 2. It appears that 30 minutes after application of the PHIAS preparation, a distinct increase in the existing moisture of the skin can be noted. Even after 120 minutes, the value corresponding to the area treated with PHIAS is clearly above control.

Statistical calculations indicate that the 30-minute value with $p<0.05$ is significantly different from control. After 120 minutes, no significant difference is left at 95% level, but the distinct action of PHIAS can still be observed from the mean values.

TABLE 1

| | Bingmer's values in pre-test (n = 4) | | | | |
| --- | --- | --- | --- | --- | --- |
| | before test | 30 min | 60 min | 90 min | 120 min |
| Control | 66.4 ± 7.3 | 64.5 ± 7.7 | 66.0 ± 7.6 | 65.2 ± 6.1 | 66.0 ± 8.0 |
| Phias | 66.4 ± 7.3 | 74.5 ± 7.7 | 73.0 ± 6.1 | 70.5 ± 8.8 | 69.0 ± 5.2 |

TABLE 2

| | Bingmer's values in main-test (n = 7) | | |
| --- | --- | --- | --- |
| | before test | 30 min | 120 min |
| Control | 77.08 ± 3.75 | 75.6 ± 3.50 | 74.8 ± 3.7 |
| Phias | 77.08 ± 3.75 | 84.4 ± 4.0* | 79.5 ± 5.0 |

*with $p < 0.05$ significantly different from control

Discussion

With the apparatus developed by BINGMER for the determination of the existing moisture of the skin's upper layers, it is possible to test the hydrating effect of cosmetics, especially on the Stratum corneum. Generally, such tests use emulsions which, together with the corresponding active substance, also supply water to the skin.

As one can see from its composition, the PHIAS preparation contains no water. The results obtained with PHIAS in BINGMER's test are all the more remarkable, because the distinct increase in the water content of the upper corneous layers can only be explained if water diffusing from the deeper cell layers of the skin and originating from the secretory elements is retained by the preparation. The effect is statistically significant after 30 minutes and produces even 120 minutes after application still distinctly higher values than control.

The results of these tests justify other experiences with galenic preparations, where PHIAS is used as a 'moisturizing factor'.

The activity of these non-saponifiable fractions has been demonstrated in the treatment of dry and cracking skin conditions. These substances, probably acting at various anatomical levels, provide the skin with a physiologically normal degree of softness and suppleness. These effects can be scientifically demonstrated and readily measured. On some skin conditions such as icthyosics, the non-saponifiable fractions of avocado oil and soy-bean oil incorporated in an adequate vehicle produce in the subject, apart from beneficial subjective phenomena, an objective effect on the dryness and roughness of the skin.

A comparative test conducted with similar preparations, where the non-saponifiable fractions had been replaced by their main constituents, i.e., β-sitosterol or a mixture of phytosterols, gave far less satisfactory results.

Another example is provided by the non-saponifiable fraction of carobe seed oil which produces a highly beneficial effect in anti-sunburn creams by minimizing the erythema caused by initial exposure to the sun rays.

Another example is embodied in the incorporation of the non-saponifiable fraction of sweet almond oil and-/or hazelnut oil in preparations intended for application to babies to cure the inflammation (diaper rash) from which they frequently suffer.

Another example is embodied in the incorporation of the non-saponifiable fraction of horsemane oil in hand creams or lotions to prevent the hands from chapping and cracking, or in optionally colored lipsticks to help prevent the lips from chapping.

The non-saponifiable fractions are obtained by conventional methods described in the literature, comprising saponifying an oil and extracting the non-saponifiable fraction (cf. for example Journal of the American Oil Chemists Society, 37, 564–567 (1960) and 39, 323–327 (1962)). The solvent used for extraction can be ethyl oxide, petroleum ether, dichloroethane, etc.

The cosmetic preparations according to the invention contain from about 0.2 to about 3% by weight of the non-saponifiable fraction based on the total weight of the end cosmetic product.

Examples of cosmetic preparations containing non-saponifiable fractions of vegetable or animal oils which may be made up in accordance with the invention include day creams, make-up bases, night creams and nourishing creams, vanishing creams, medicinal creams, e.g., vitamin creams, acid creams, hormone creams, protective creams, cold cream, creams and milks for removing make-up, toilet lotions, face creams, masking creams, foundation creams, creams, milks and oils for the hands, body creams and milks, milks, oils, lotions, aerosol lathers, anti- and post-solar creams, lipsticks, oils for the body, creams, milks and baby-care products (powders, oils), deodorants in the form of sticks, powders, emulsions, creams, lotions, shaving creams, after-shave lotions, creams and foams.

Some examples of formulations from the preceding list are given below with the percentages indicated by weight. In addition, there is in each case the quantity of oil that would be necessary to obtain a quantity of the non-saponifiable fraction equivalent to that mentioned in each example. It will be readily noted that to obtain a formulation with a corresponding amount of non-saponifiable fraction, an inordinate amount of the oil would have to be included.

EXAMPLE 1

| Hand cream: | g |
|---|---|
| non-saponifiable fraction of horse-mane oil | 0.5 |
| beeswax | 15 |
| mineral oil 65/75 | 25 |
| cetyl alcohol | 10 |
| lanolin | 5 |
| sweet almond oil | 5 |
| sorbitan monostearate | 4 |
| sorbitan sesquioleate | 4 |
| preservative perfume and water | quantity sufficient for 100 |

To obtain an equivalent amount of non-saponifiable fraction it would have been necessary to use 250 g of horse-mane oil as such.

EXAMPLE 2

| Make-up removing milk for dry skins: | g |
|---|---|
| non-saponifiable fraction of avocado oil | 0.1 |
| non-saponifiable fraction of soya-bean oil | 0.2 |
| sweet almond oil | 8 |
| glycerol monostearate | 3 |
| cetyl alcohol | 2 |
| oxyethylenated sorbitan oleate | 2 |

| Make-up removing milk for dry skins: -continued | g |
|---|---|
| oxyethylenated lauric ether | 2 |
| preservatives perfume and water | quantity-sufficient for 100 |

To obtain the same proportions of non-saponifiable fractions with the oils as such, it would have been necessary to use 10 g of avocado oil and 40 g of soya-bean oil, the rest of the formulation being identical.

The product obtained in this case would have been a very oily and highly unstable cream rather than a milk in view of the excessive amount of oil that would have been present in it.

EXAMPLE 3

| Protective cream for dry skins: | g |
|---|---|
| non-saponifiable fraction of avocado oil | 0.35 |
| non-saponifiable fraction of soya-bean oil | 0.70 |
| avocado oil | 10.00 |
| monostearate | 5.00 |
| cetyl alcohol | 4.00 |
| propylene glycol | 5.00 |
| lanette | 6.00 |
| polyoxyethylenated lauric ether | 3.00 |
| sorbitan sesquioleate | 3.00 |
| preservative perfume, water | quantity sufficient for 100.00 |

To obtain the same proportions of non-saponifiable fractions with the oils as such, it would have been necessary to use 35 g of avocado oil and 140 g of soya-bean oil, the rest of the formulation being identical.

EXAMPLE 4

| Face lotion: | g |
|---|---|
| non-saponifiable fraction of sweet almond oil | 0.5 |
| triethanolamine lauryl sulphate | 5 |
| propylene glycol | 10 |
| witch-hazel water | 20 |
| preservative rose water | quantity sufficient for 100 |

To obtain the same proportion of non-saponifiable fraction with the oil as such, it would have been necessary to use 100 g of sweet almond oil which would have resulted in the formation of a product in the form of an oil rather than an aqueous lotion for the preparation made up to 100 g.

EXAMPLE 5

| Anti-sun oil: | g |
|---|---|
| non-saponifiable fraction of carob bean oil | 1.00 |
| olive oil | 20.00 |
| sun filter | 2.0 |
| anti-oxidant perfume paraffin oil | quantity sufficient for 100.00 |

To obtain the same proportion of non-saponifiable fraction with the oil as such, it would have been necessary to use 30 g of carob bean oil. Although this preparation is theoretically possible, it would be necessary to modify the proportions of the other two constituent oils of the formulation. A highly oxidisable and drying preparation would have been obtained. It would, therefore, be unsuitable for use.

EXAMPLE 6

| Lipstick: | | g |
|---|---|---|
| non-saponifiable fraction of cod-liver oil | | 1 |
| beeswax | | 10 |
| ozocerits | | 24 |
| carnauba wax | | 8 |
| solid paraffin | | 8 |
| liquid paraffin | | 22 |
| lanolin | | 9 |
| titanium dioxide | | 1 |
| colorants | quanity | |
| solvents | sufficient | |
| aromatisers | for | 100 |

To obtain the same proportion of non-saponifiable fraction, it would have been necessary to use 100 g of cod-liver oil, the rest of the formulation being identical.

The invention has been shown and described in preferred form only, and by way of example, and many variations may be made in the invention which will still be comprised within its spirit. It is understood, therefore, that the invention is not limited to any specific form or embodiment except insofar as such limitations are included in the appended claims.

I claim:

1. A topically appliable cosmetic composition, in the form of a protective cream for dry skins, for creating an increase in the moisture content of human skin consisting essentially of
    a cosmetic composition containing the non-saponifiable fraction extracted from soya-bean oil and avocado oil, with the weight ratio of said soya-bean oil non-saponifiable fraction to said avocado oil non-saponifiable fraction being about 2 to 1, and said non-saponifiable fraction being from about 0.2% to 3% by weight based upon the total composition weight, and
    the balance of said composition being hexyl laurate and avocado oil.

2. A method for creating an increase in the moisture content of human skin consisting essentially of
    topically applying to said skin, in the form of a protective cream of dry skins, an effective amount of a topically appliable cosmetic composition consisting essentially of
    a cosmetic composition containing the non-saponifiable fraction extracted from soya-bean oil and avocado oil, with the weight ratio of said soya-bean oil non-saponifiable fraction to said avocado oil non-saponifiable fraction being about 2 to 1, and said non-saponifiable fraction being from about 0.2% to 3% by weight based upon the total composition weight, and
    the balance of said composition being a cosmetic carrier suitable for topical application to said human skin.

3. A method for creating an increase in the moisture content of human skin consisting essentially of
    topically applying to said skin, in the form of a protective cream for dry skins, an effective amount of a topically appliable cosmetic composition consisting essentially of
    a cosmetic composition containing the non-saponifiable fraction extracted from an oil selected from the group consisting of horse mane oil, sweet almond oil, carob bean oil and cod-liver oil, and said non-saponifiable fraction being from about 0.2% to 3% by weight based upon the total composition weight, and
    the balance of said composition being a cosmetic carrier suitable for topical application to said human skin.

4. The method of claim 3, wherein said non-saponifiable fraction is extracted from horse mane oil.

5. The method of claim 3, wherein said non-saponifiable fraction is extracted from sweet almond oil.

6. The method of claim 3, wherein said non-saponifiable fraction is extracted from carob bean oil.

7. The method of claim 3, wherein said non-saponifiable fraction is extracted from cod-liver oil.

* * * * *